United States Patent
Gisler et al.

(10) Patent No.: US 9,529,762 B2
(45) Date of Patent: Dec. 27, 2016

(54) SELF POWERED SERIAL-TO-SERIAL OR USB-TO-SERIAL CABLE WITH LOOPBACK AND ISOLATION

(75) Inventors: Scott Gisler, Allendale, NJ (US); Dave Arndt, North Caldwell, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 2317 days.

(21) Appl. No.: 10/872,779

(22) Filed: Jun. 22, 2004

(65) Prior Publication Data
US 2005/0001179 A1    Jan. 6, 2005

Related U.S. Application Data

(60) Provisional application No. 60/483,230, filed on Jun. 30, 2003, provisional application No. 60/483,247, filed on Jun. 30, 2003.

(51) Int. Cl.
*A61B 5/00* (2006.01)
*G06F 13/40* (2006.01)
*G06F 1/26* (2006.01)
*A61B 5/0428* (2006.01)
*H04B 10/80* (2013.01)
(Continued)

(52) U.S. Cl.
CPC ....... *G06F 13/4072* (2013.01); *A61B 5/04282* (2013.01); *A61B 5/04286* (2013.01); *G05B 23/0216* (2013.01); *G05B 23/0272* (2013.01); *G06F 1/266* (2013.01); *G06F 11/221* (2013.01); *G06F 11/323* (2013.01); *H01L 31/16* (2013.01); *H03K 17/78* (2013.01); *H04B 10/802* (2013.01); *A61B 5/14532* (2013.01);
(Continued)

(58) Field of Classification Search
CPC ...................................................... G06F 1/266
See application file for complete search history.

(56) References Cited

U.S. PATENT DOCUMENTS 3,742,947 A    7/1973   Hashem
4,498,716 A *   2/1985   Ward .............................. 439/55
(Continued)

FOREIGN PATENT DOCUMENTS

DE    41 13 920    11/1992
GB    2 349 283    10/2000
(Continued)

OTHER PUBLICATIONS

Therasense, FreeStyle Data Management [online] [retrieved on Jun. 25, 2003]. Retrieved from Internet: <URL: http://www.therasense.com/freestyle/datamanagement/index.html>.
(Continued)

*Primary Examiner* — William Thomson
*Assistant Examiner* — Davin Sands
(74) *Attorney, Agent, or Firm* — Dickinson Wright PLLC

(57) ABSTRACT

The cable for a medical device is an optically isolated serial transmission cable, used to connect a base device with a serial port, or the like, to a medical device. In an alternate embodiment of the invention, the invention enables auto detection of the cable. The base device is used to power the cable electronics. In another embodiment of the present invention, the interface cable is also supported by graphical and text message display that assists users in connecting the cable to both the medical device and a base device.

23 Claims, 12 Drawing Sheets

(51) Int. Cl.
    *G06F 11/22*     (2006.01)
    *G06F 11/32*     (2006.01)
    *G05B 23/02*     (2006.01)
    *H03K 17/78*     (2006.01)
    *H01L 31/16*     (2006.01)
    *A61B 5/145*     (2006.01)

(52) U.S. Cl.
    CPC ... *A61B 2560/045* (2013.01); *A61B 2562/222* (2013.01); *H01R 2201/12* (2013.01)

(56) References Cited

U.S. PATENT DOCUMENTS

| | | | |
|---|---|---|---|
| 4,908,819 A * | 3/1990 | Casady et al. | 370/204 |
| 4,976,681 A | 12/1990 | Magro | |
| 5,128,962 A * | 7/1992 | Kerslake et al. | 375/220 |
| 5,481,741 A * | 1/1996 | McKaskle et al. | 345/522 |
| 5,544,319 A * | 8/1996 | Acton et al. | 709/246 |
| 5,566,339 A * | 10/1996 | Perholtz et al. | 713/340 |
| 5,691,898 A * | 11/1997 | Rosenberg et al. | 700/85 |
| 5,793,366 A * | 8/1998 | Mano et al. | 715/839 |
| 5,809,226 A * | 9/1998 | Baldwin et al. | 714/43 |
| 5,938,754 A * | 8/1999 | Edwards et al. | 710/305 |
| 6,602,191 B2 * | 8/2003 | Quy | 600/300 |
| 6,651,177 B1 * | 11/2003 | Rantze et al. | 713/300 |
| 6,686,838 B1 * | 2/2004 | Rezvani et al. | 340/506 |
| 6,730,025 B1 * | 5/2004 | Platt | 600/300 |
| 6,751,253 B1 * | 6/2004 | Walance et al. | 375/220 |
| 6,907,283 B2 * | 6/2005 | Carter et al. | 600/509 |
| 7,200,510 B2 * | 4/2007 | Yasuda et al. | 702/119 |
| 7,299,088 B1 * | 11/2007 | Thakor et al. | 600/544 |
| 2001/0047125 A1 * | 11/2001 | Quy | 600/300 |
| 2002/0007198 A1 * | 1/2002 | Haupert et al. | 607/30 |
| 2002/0105409 A1 * | 8/2002 | Nakamitsu et al. | 340/3.1 |
| 2002/0126091 A1 * | 9/2002 | Rosenberg et al. | 345/161 |
| 2002/0143487 A1 * | 10/2002 | Yasuda et al. | 702/119 |
| 2003/0176183 A1 * | 9/2003 | Drucker et al. | 455/414.1 |
| 2003/0225317 A1 * | 12/2003 | Schell | 600/300 |
| 2004/0034496 A1 * | 2/2004 | Correll et al. | 702/127 |
| 2004/0098515 A1 * | 5/2004 | Rezvani et al. | 709/400 |
| 2004/0186689 A1 * | 9/2004 | Chu et al. | 702/186 |

FOREIGN PATENT DOCUMENTS

| | | |
|---|---|---|
| GB | 2349283 A | 10/2000 |
| JP | 48-32390 | 4/1973 |
| JP | H1027038 A | 1/1998 |
| JP | H10307646 A | 11/1998 |
| JP | 2000-148303 | 5/2000 |
| JP | 2000-200250 | 7/2000 |
| JP | 2002318614 A | 10/2002 |
| JP | 2003-046509 | 2/2003 |

OTHER PUBLICATIONS

Therasense, FreeStyle Tracker [online] [retrieved on Jun. 25, 2003]. Retrieved from Internet: <URL: http://www.therasense.com/tracker/product/index_flash.asp>.

Therasense, FreeStyle Blood Glucose Monitoring System [online] [retrieved on Jun. 25, 2003]. Retrieved from Internet: <URL: http://www.therasense.com/freestyle/productdemo/index.html>.

iMetrikas, Medicompass [online] [retrieved on Sep. 23, 2004]. Retrieved from Internet: <URL: http://www.imetrikus.com/products.asp>.

* cited by examiner

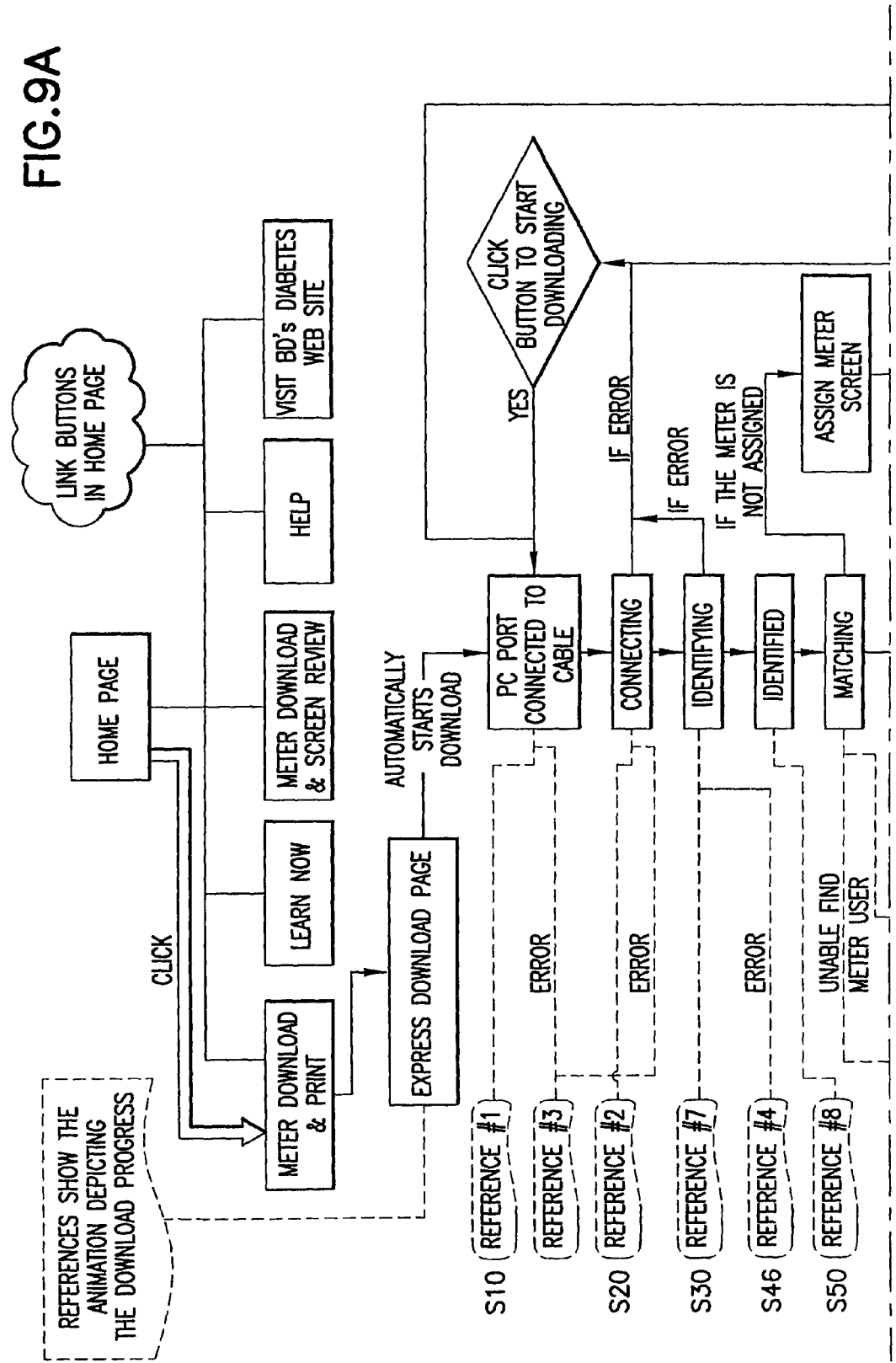

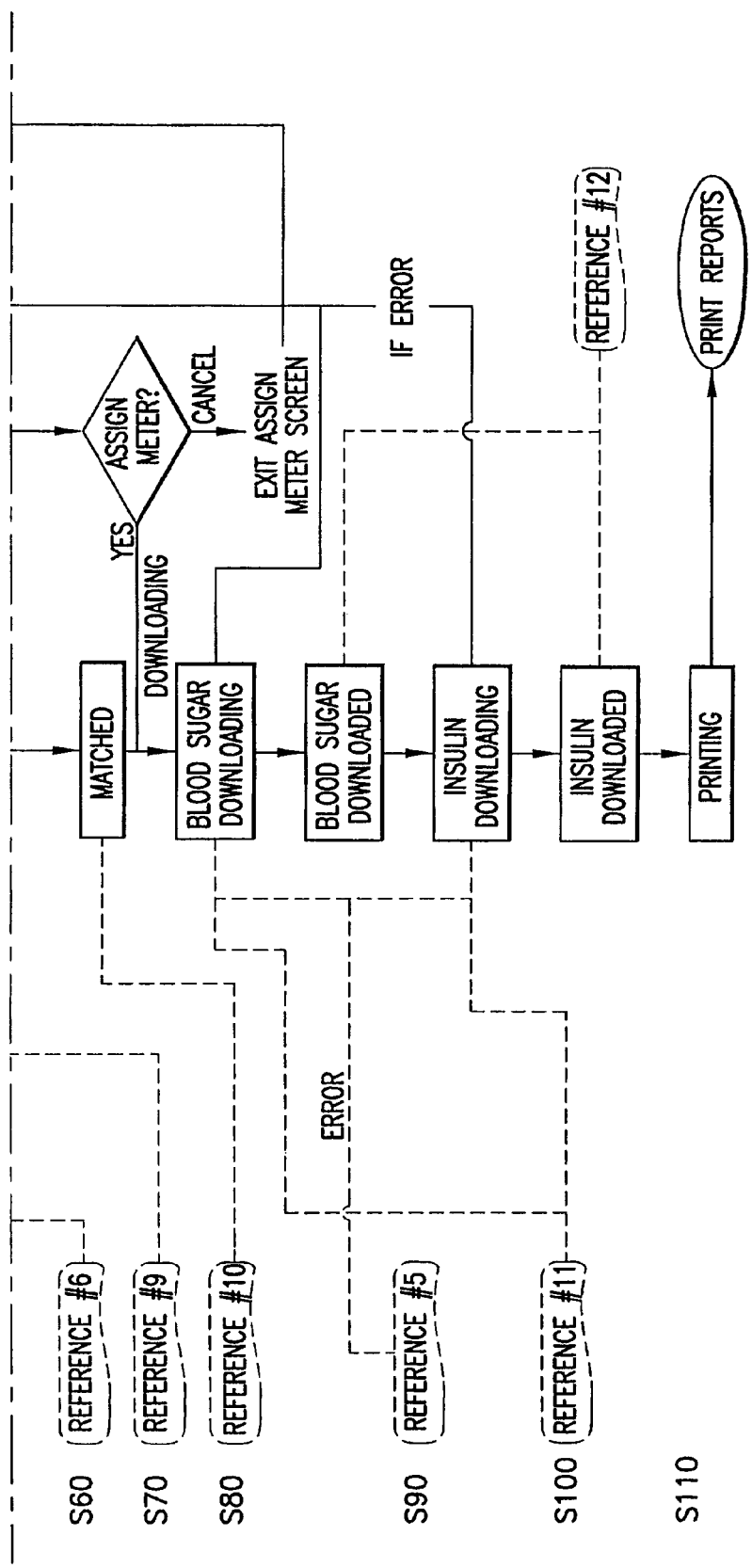

REFERENCE FOR METER DOWNLOAD

1-PC PORT CONNECTED TO CABLE

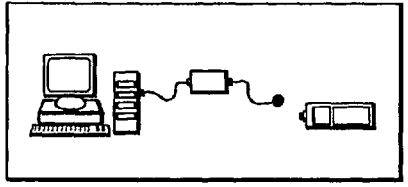

2-CONNECTING

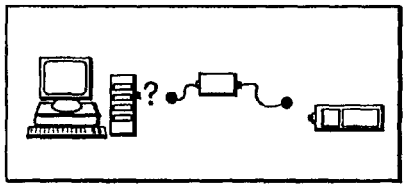

3-COULD NOT FIND CONNECTION ON ANY PORT

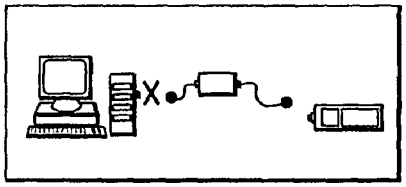

4-COULD NOT IDENTIFY METER ON ANY PORT

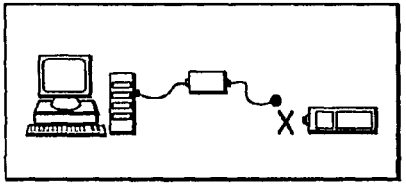

5-THE OPERATION COULD NOT COMPLETE- CHECK THE CABLE CONNECTION WITH METER

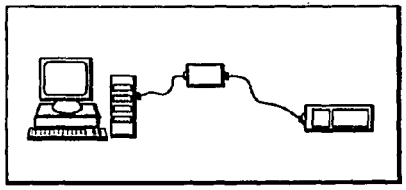

6-UNABLE FIND METER USER____ ASSIGN METER USER

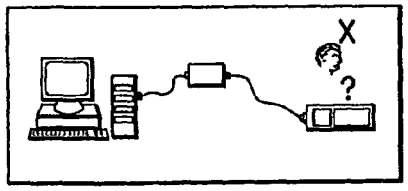

7-IDENTIFYING

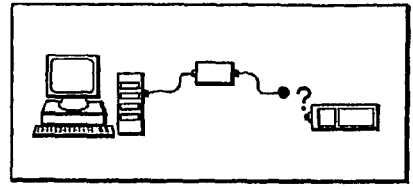

8-IDENTIFIED

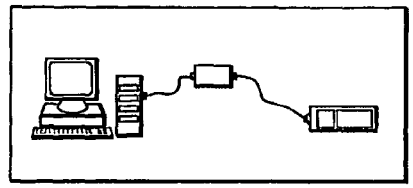

9-MATCHING METER TO ASSIGNED USER

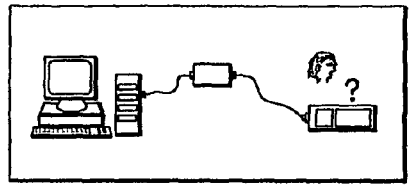

10-MATCHING ASSIGNED USER TO METER

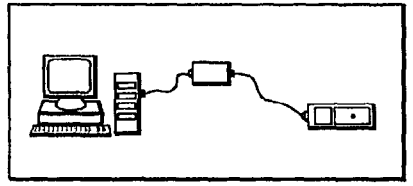

11-ANIMATED UPLOADING

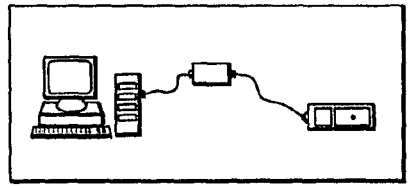

12-UPDATING THE DATA

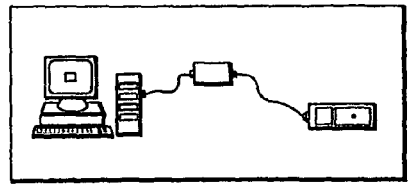

FIG.10

SELF POWERED SERIAL-TO-SERIAL OR USB-TO-SERIAL CABLE WITH LOOPBACK AND ISOLATION

This application claims the benefit of U.S. Provisional Application No. 60/483,230 filed Jun. 30, 2003, and U.S. Provisional Application No. 60/483,247 filed Jun. 30, 2003, the entire contents of each of said applications being incorporated herein by reference. Related subject matter is disclosed and claimed in a concurrently filed U.S. nonprovisional patent application of Paul Upham et al. entitled "Method and Apparatus for Managing Data Received From a Medical Device", the entire content of which is incorporated herein by reference.

FIELD OF THE INVENTION

An aspect of the present invention relates to interface cables for medical devices which communicate with base devices. Examples of a base device are a standard personal computer or another device with at least one serial port or Universal Serial Bus (USB) port. More particularly, the present invention relates to a data transfer cable for use with a glucose monitor for communications with a personal computer. In addition, another aspect of the present invention relates to graphical status displays for connecting a personal computer to a medical device using a data transfer cable. In particular, this aspect of the present invention relates to a system for generating a graphical display to assist a user in connecting a medical device to a base device.

BACKGROUND OF THE INVENTION

In the present healthcare environment, it is desirable to download data from devices regularly used by patients to other devices, such as PCs and the like, so that the data may be analyzed. Treatment of various medical conditions may then be optimized by analysis of the data. The transfer of information needs to occur without undue strain on the patient's medical device, such as a drain on the medical device battery, as well as maintaining safe conditions including electrical isolation, for the patient. Interface cables have the problem of maintaining isolation of the patient from electrical hazards presented by having a cable in electrical contact with powered devices, such as a PC, that may present a hazard to the patient. In the past, infrared communications have been proposed as a solution to the isolation problem; however, this puts an undue strain on the battery of the medical device. A medical device may be a device that monitors a medical condition and collects data, such as a blood glucose monitor. Alternatively, a medical device could also be a device that administers treatment to a patient in response to a treatment regime determined by a healthcare professional, such as a drug therapy regime for the treatment of diabetes. Finally, a medical device could be a combination device that both monitors a medical condition and administers a treatment in response to the medical conditions monitored.

Normally when a medical device is connected to a serial port, such as a standard serial or USB port on a base device, the user must select the type of serial port to which the device is connected. Also, when a base device has a plurality of standard serial ports, the user must configure the base device to communicate on the particular serial port to which the medical device is connected, which can cause confusion. It would be advantageous for the base device to have the ability to detect the presence of a medical device so that it may begin downloading data or performing other processes. In addition, it is not desirable to require the medical device to use a standard serial communication interface, which involves a complex connection. Such a connection may possibly require using a secondary connector on the medical device, thereby increasing costs and complexity. What is needed is an interface cable that provides isolation, automatic detection and a simple connection to the medical device.

The automatic detection feature has great advantages in a healthcare setting where multiple vendors' software and cables are used. In such a setting, it is very annoying and tedious for the healthcare provider to figure out which port they are connected to every time they connect or re-connect a cable. Some serial connecting devices tie the request to send (RTS) connection and clear to send (CTS) connection together and the data terminal ready (DTR) connection and data set ready (DSR) connection together, this allows the software to determine that a cable is connected to a particular port, but does not identify to which vendor the cable belongs. Also on some computers this tie back scenario causes the power to be sent back to the PC and not to power any internal circuitry of the cable. A clear solution that automatically detects the identity of the connecting device would help solve the above problems, save time, reduce undue frustration, and facilitate quicker exchanges of patient data.

The computer skills among persons required to use various medical devices vary greatly. For instance, persons of all ages may have diabetes, the onset of which can happen at a very early age or much later in life, so there is a wide variety of computer proficiency among diabetes patients and their families. Connecting a medical device to a cable or connecting device and then to a base device can be tedious particularly when neither the medical device nor the base device provide any indication whether a connection problem exists or on which end the problem may lie. Presently, there does not exist a connecting device for medical devices that includes an animated meter-to-connecting device-to-PC connection graphics and text messaging display system to assist the user in properly connecting their medical device to a PC.

Other meter download software programs have some graphics associated with the meter download process but none of them provide the combined state detection, graphics, and messages of an embodiment of the present invention.

SUMMARY OF THE INVENTION

The aforementioned disadvantages are overcome, and other advantages are realized, in a system and method according to an embodiment of the present invention. The present invention provides a simple interface between medical device and base device, which provides power from the base device to the cable, thereby isolating the medical device. The isolation circuit prevents the user from being subject to the possible electrical hazards presented by the connection to the base device.

In addition, the cable insures that the base device is able to identify the cable as belonging to a medical device that uses the specific software applications associated with the medical device. Automatic detection of the serial port address is accomplished by a loopback feature, which polls the ports of the base device to identify where the cable is located. This allows the base device to automatically identify the cable without a meter connected.

Furthermore, the connectors of the cable are standard connectors familiar to most users, which make connecting the cable to a base device and to a medical device simple. To facilitate even greater ease of use, the connectors to the base device are USB connectors as well as well known serial connectors, such as RS-232C connectors.

According to an embodiment of the present invention, graphics and text messages provide a way to pinpoint specific problems that may be preventing a successful connection of the cable to either the base device or the medical device. According to another aspect of the present invention, animations and messages provide a visual indicator that there is some activity between the base device, cable and the medical device.

BRIEF DESCRIPTION OF THE DRAWINGS

The invention will be more readily understood with reference to the attached drawings figures, in which:

FIG. 9 is a flowchart showing the steps of connecting the cable to a base device and a medical device; and FIG. 10 shows exemplary graphical and text messages that a user may receive during each of the steps in the flowchart of FIG. 9.

In the drawing figures, it will be understood that like numerals refer to like features and structures.

DETAILED DESCRIPTION OF THE PREFERRED EMBODIMENTS

Preferred embodiments of the present invention will now be described with reference to the attached drawing figures.

Figure 1:
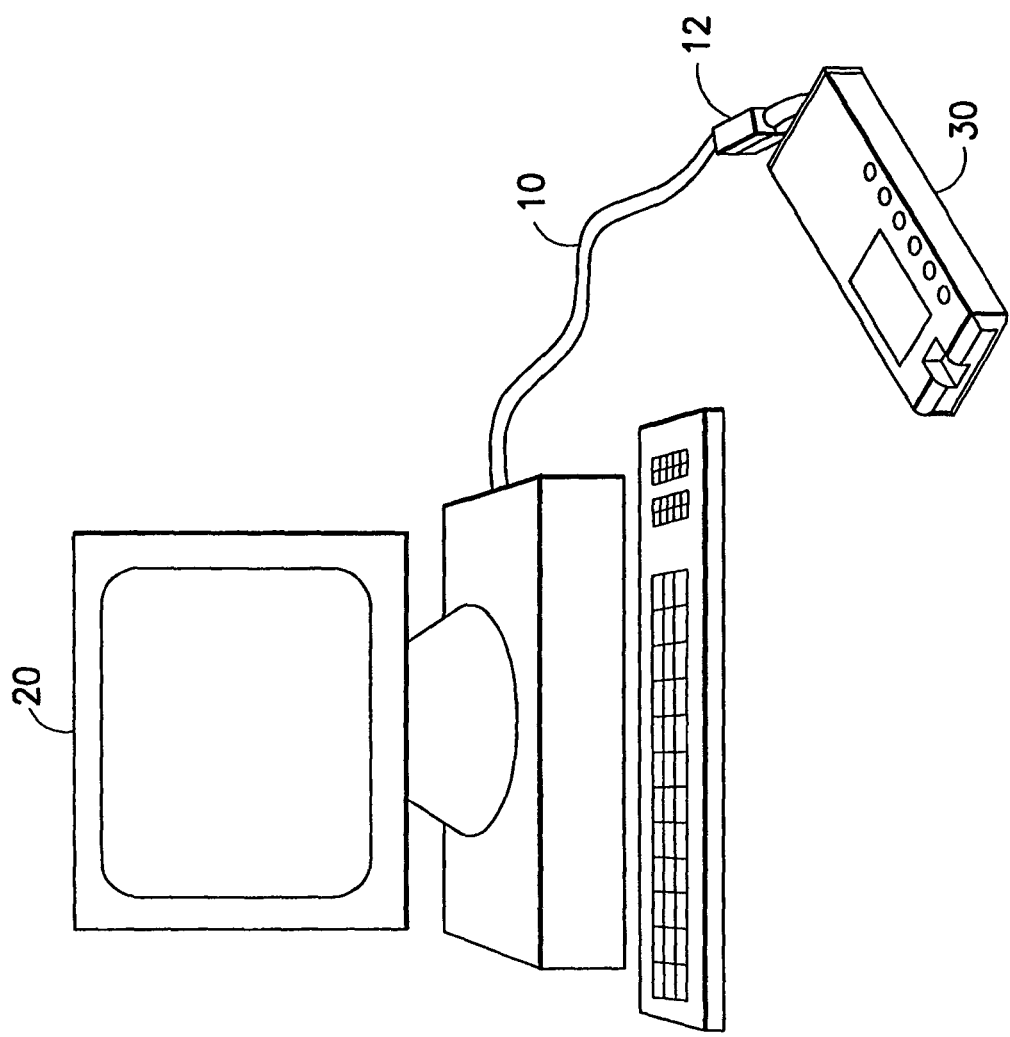
FIG. 1 illustrates a cable according to an embodiment of the present invention in use connecting a base device and a medical device.

Referring to FIG. 1, which shows an embodiment of the invention, where the interface cable 10 for the portable medical device 30 is a self-powered serial to serial optically isolated half duplex serial transmission cable. Cable 10 is preferably intended for half duplex operation. However, a simple change in the electronics portion 12 enables the cable 10 for full duplex operation, which later will be in more detail. Cable 10 is used to connect the base device 20 which could be a personal computer or similar device with a serial port (Standard or USB) to medical device 30. The cable has an electronics portion 12 which may house the circuitry that enables operation of the invention. The cable 10 connection to the medical device 30 is a connector that connects to the data port of the medical device 30, which in the case of a blood glucose monitor would be the test strip slot.

Figure 2:
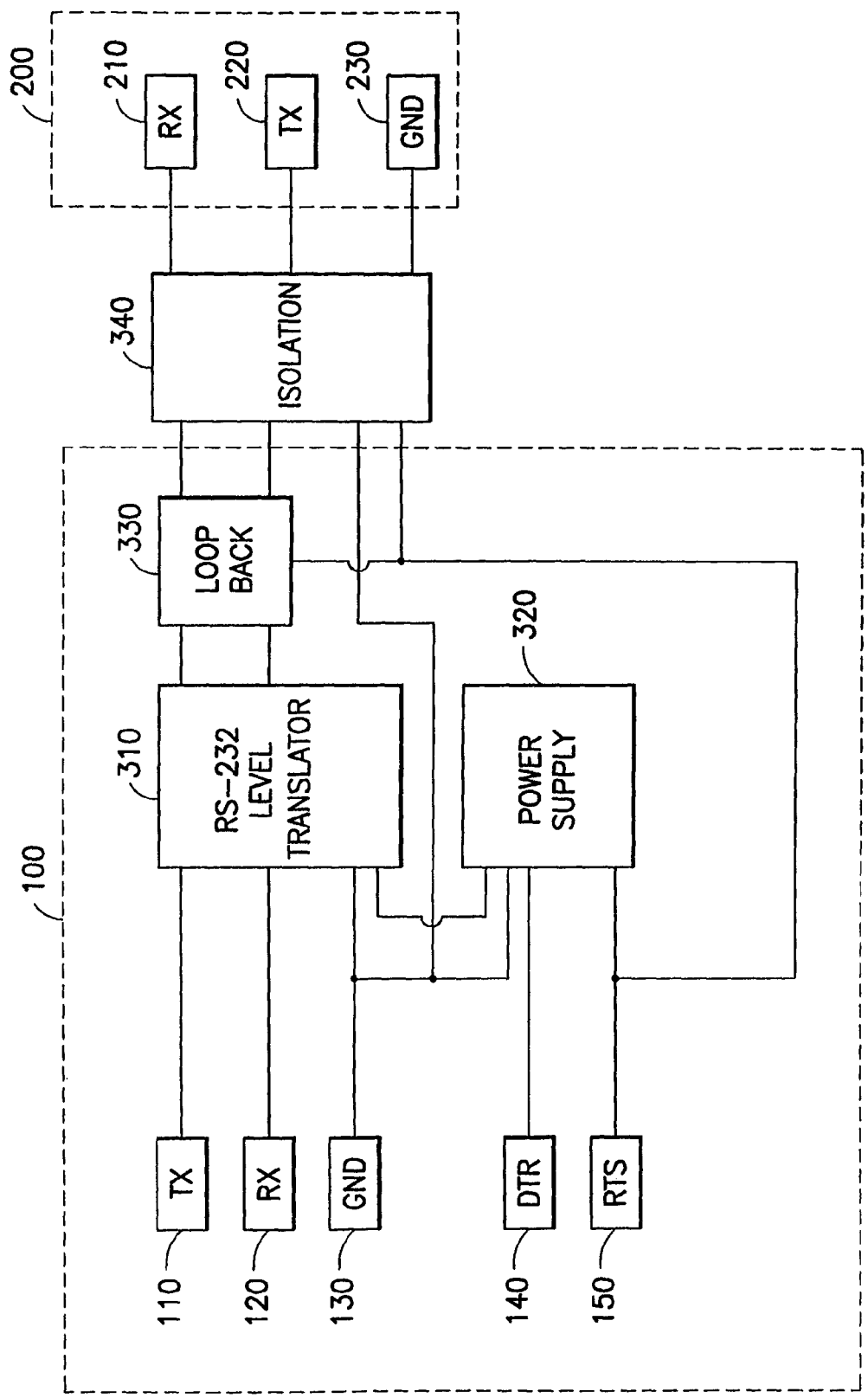
FIG. 2 shows a block diagram of a cable according to an embodiment of the present invention.

Now referring to FIG. 2, which shows a block diagram of the operation of cable 10. Medical device 30 preferably contains isolated side 200, while non-isolated side 100 is preferably contained within base device 20. Cable 10 comprises two ends or sides, an isolated side 200 of cable 10 and a non-isolated side 100. Each side 100, 200 is separated by an isolation barrier 340, which preferably comprises standard optical isolation techniques known in the art. On isolated side 200, the TX line 220 is used to power the electronics of cable 10. If full duplex signaling were allowed, the RX line 210 to medical device 30 would receive a similar signal or a corrupted signal from TX line 110 and would cause problems in the communications. Five of the nine standard serial cable lines are used in cable 10. Cable 10 uses the following lines TX line 110, RX line 120, GND line 130, DTR line 140, and RTS line 150. The DTR line 140 is used to power the non-isolated side 100 of the cable 10 when held high. When the DTR line 140 is low, DTR line 140 does not power the circuit. The RTS line 150 is used for multiple purposes. When RTS line 150 is low, the loop back circuit 330 is signaled to execute a loop back feature which echoes back any data sent from the PC serial output to its serial input and powers down any unnecessary circuitry on the non-isolated side 100 of the isolation barrier. This is accomplished by removing power from photocoupler 155, which is in isolation circuit 340 (See FIG. 4B for more detail). When the RTS line 150 is high, it is used to power the non-isolated side 100 of cable 10, put cable 10 in straight through mode to medical device 30, and power up the circuitry on isolated side 200 of the isolation barrier 340.

The following describes the operation of cable 10 input control lines. When the software application of base device 20 starts it makes RTS line 150 and DTR line 140 high in order to detect the serial cable 10 on a port automatically. After the serial cable is detected, RTS line 150 should be made low and DTR line 140 should be left high. This allows the software application of base device 20 to echo characters back in order to identify cable 10 as the cable 10 of the present invention is connected to base device 20. It also removes power from any unnecessary circuitry on the isolated side 200 of isolation barrier 340, which reduces the drain on the battery within medical device 30. When the base device 20 is ready to send data, the base device 20 makes RTS line 150 high. Then base device 20 transmits and receives data in a half duplex mode. Once the communication is complete, RTS line 150 is preferably made low in order to conserve the battery power of the medical device 30. If more data is requested later, the above procedure is preferably repeated. If the base device 20 is done communicating with the medical device 30, the base device 20 makes DTR line 140 low.

Medical device 30 should be disconnected from cable 10 when not in use to increase battery life of medical device 30. A warning message may be presented by the software of base device 20 after the download to indicate to the user to disconnect medical device 30. In addition, a small delay could be added when switching the state of the RTS line 150 and DTR line 140 in order to allow them to settle into their steady states. This delay should be approximately on the order of 100 ms. In addition, it is desirable for the microprocessor of medical device 30 to block the measurement portion of the microprocessor of medical device 30 while cable 10 is connected to medical device 30. This is accomplished by a signal from cable 10 to medical device 30, which prohibits measurements from taking place in medical device 30.

Figure 4A:
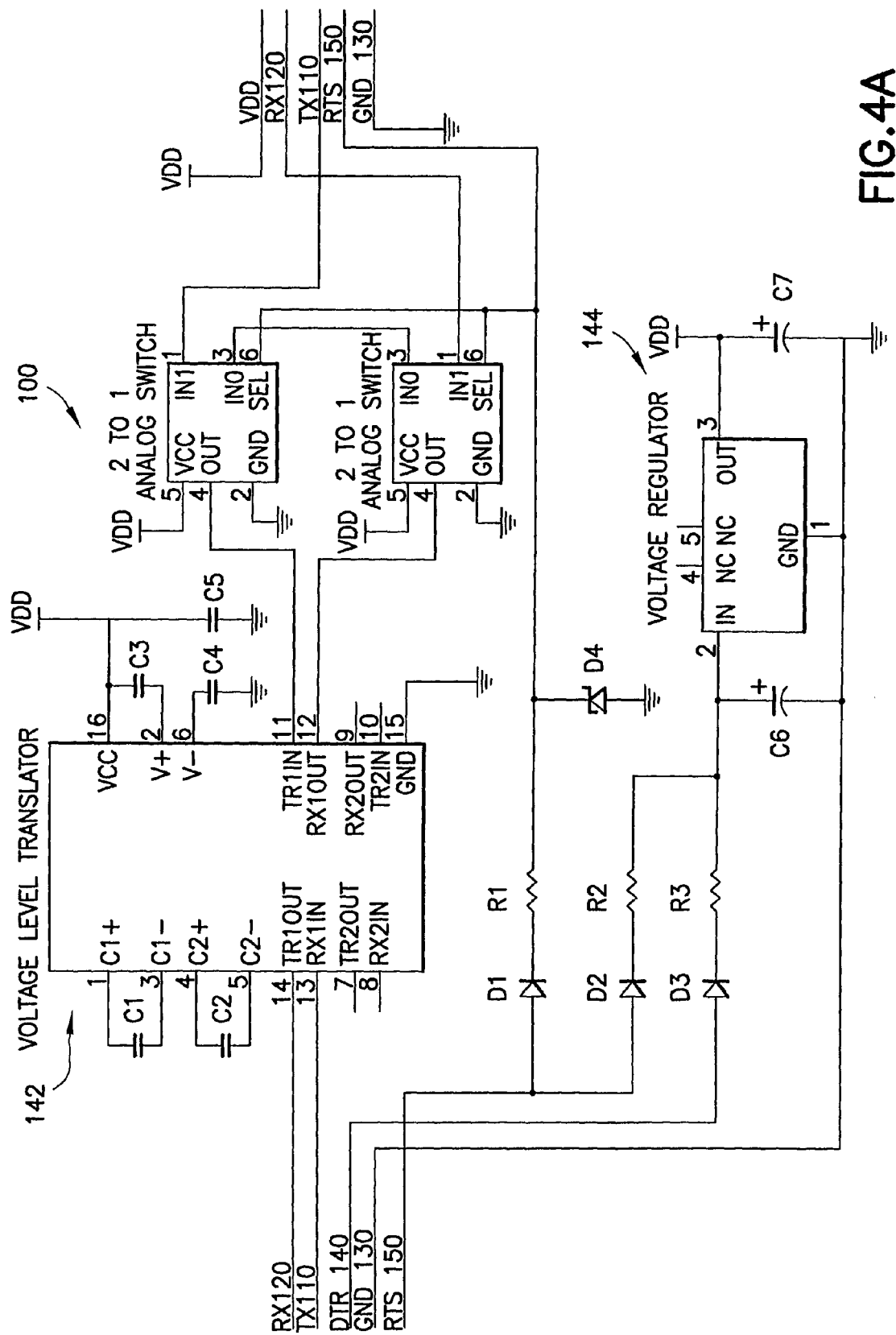
FIG. 4A shows exemplary serial-connection circuitry of the cable shown in FIG. 2.
Figure 4B:
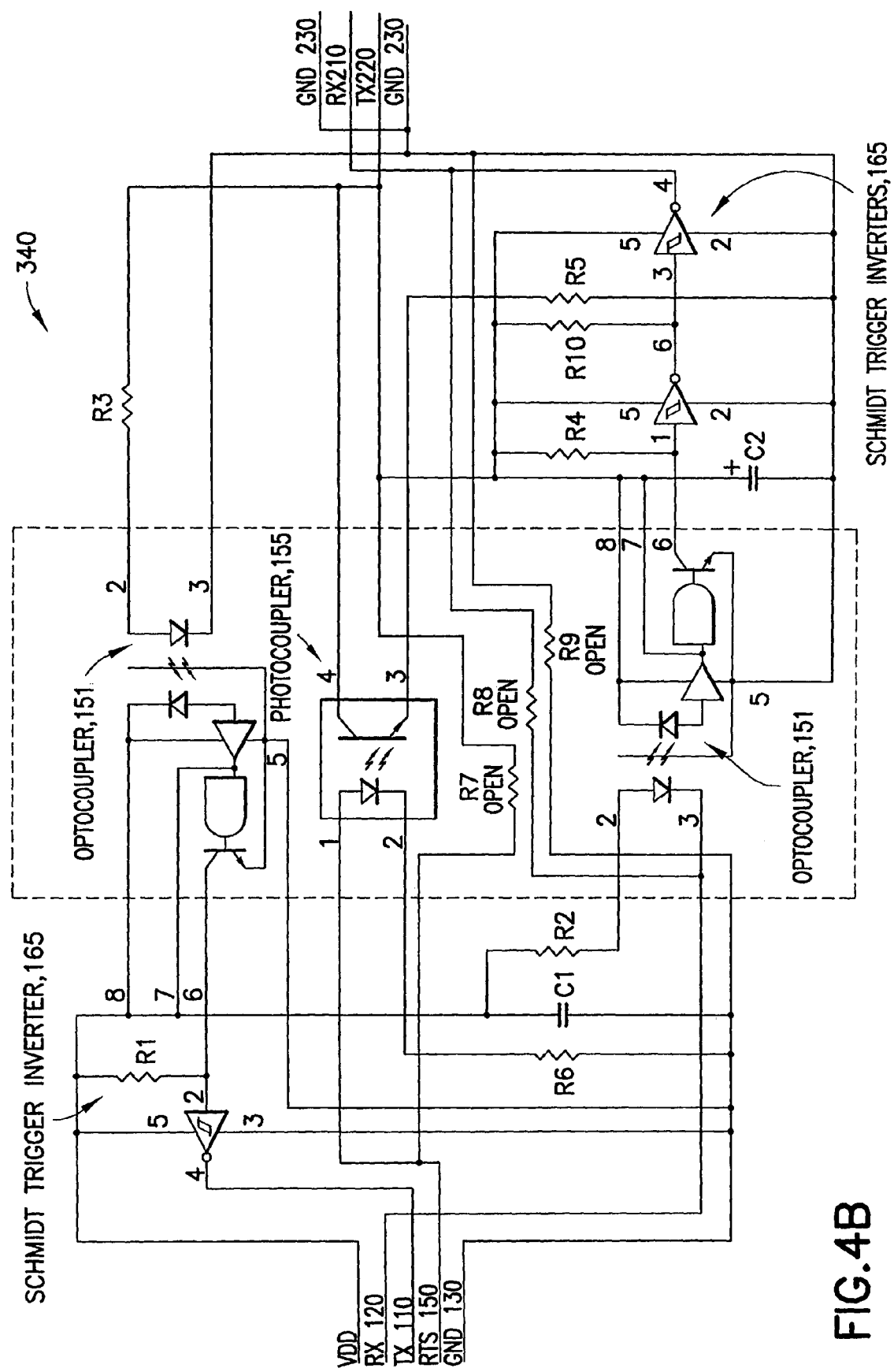
FIG. 4B shows the isolation circuit and the connections to the medical device common to both of the cables shown in FIGS. 2 and 3.

FIGS. 4A and 4B are circuit diagrams of the entire cable shown in FIG. 2. In FIG. 4A, the base device 20 makes the RTS 150 and DTR 140 lines high state, which causes a voltage regulator 144 to generate a regulated power supply voltage VDD. This voltage VDD is supplied to a standard RS-232 voltage level translator 142 with built in electrostatic discharge protection. Control lines DTR 140 or RTS 150 separately can also provide enough power to generate a regulated power supply voltage VDD from voltage regulator 144. Control line RTS 150 is level translated by the use of a diode to reduce its voltage level to an acceptable voltage. Two analog switches or multiplexers 144, 146 are used to direct the TX 110 signal back to the RX 120 signal or straight through to the TX 210 of the connected device. In FIG. 4B, RTS 150 also turns on and off photocoupler 155 within isolation barrier 340 to enable or disable power a section of the circuitry on the isolated side of the circuit. This is used due to the fact that the TX 220 line of the connected device is supplying power to the isolated side of the circuit, so the less circuitry powered the less draw on the connected device. In FIG. 4B, Schmidt triggered inverters 165 are used to clean or sharpen the signals received across the isolation barrier in order to be received properly by either device 100, 200.

Figure 3:
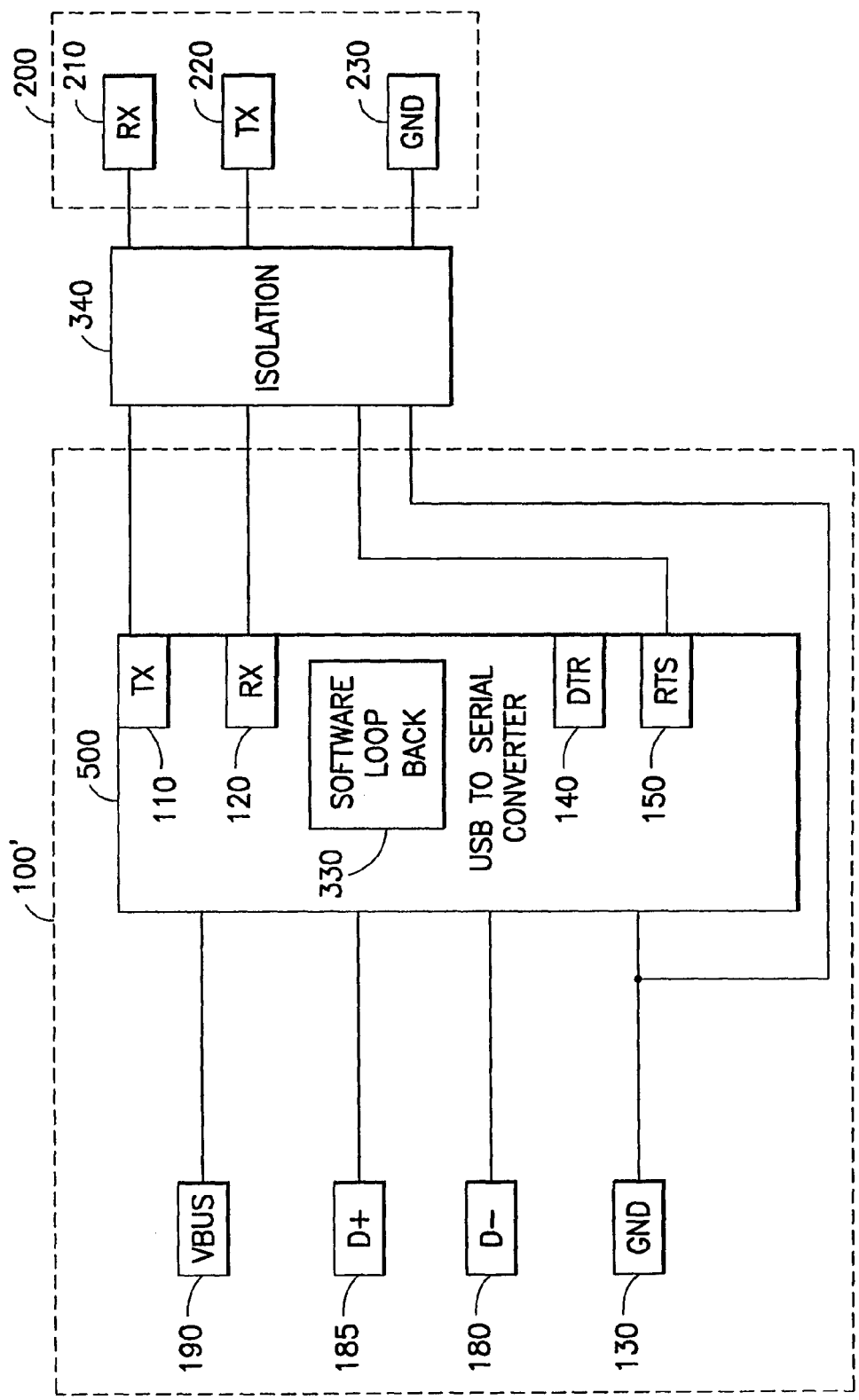
FIG. 3 shows a block diagram of a cable according to an alternate embodiment of the present invention.

FIG. 3 illustrates a USB device within base device 20 according to an embodiment of the present invention. One difference between the previous embodiment and the current embodiment is that in the VBUS line 190 and GND line 130 from the USB port within base device 20 are used to power the circuit on non-isolated side 100'. In addition, shown in more detail in FIG. 5, a microprocessor 510 or a logic circuit within a USB-to-serial converter 500 is used to translate the USB data stream to a serial data stream by a USB-to-serial converter 500. In this embodiment, the loopback feature is implemented via software programming within the microprocessor 510 of the USB to serial converter 500. All other control lines are preferably activated the same way as in the previous embodiment.

Figure 5:
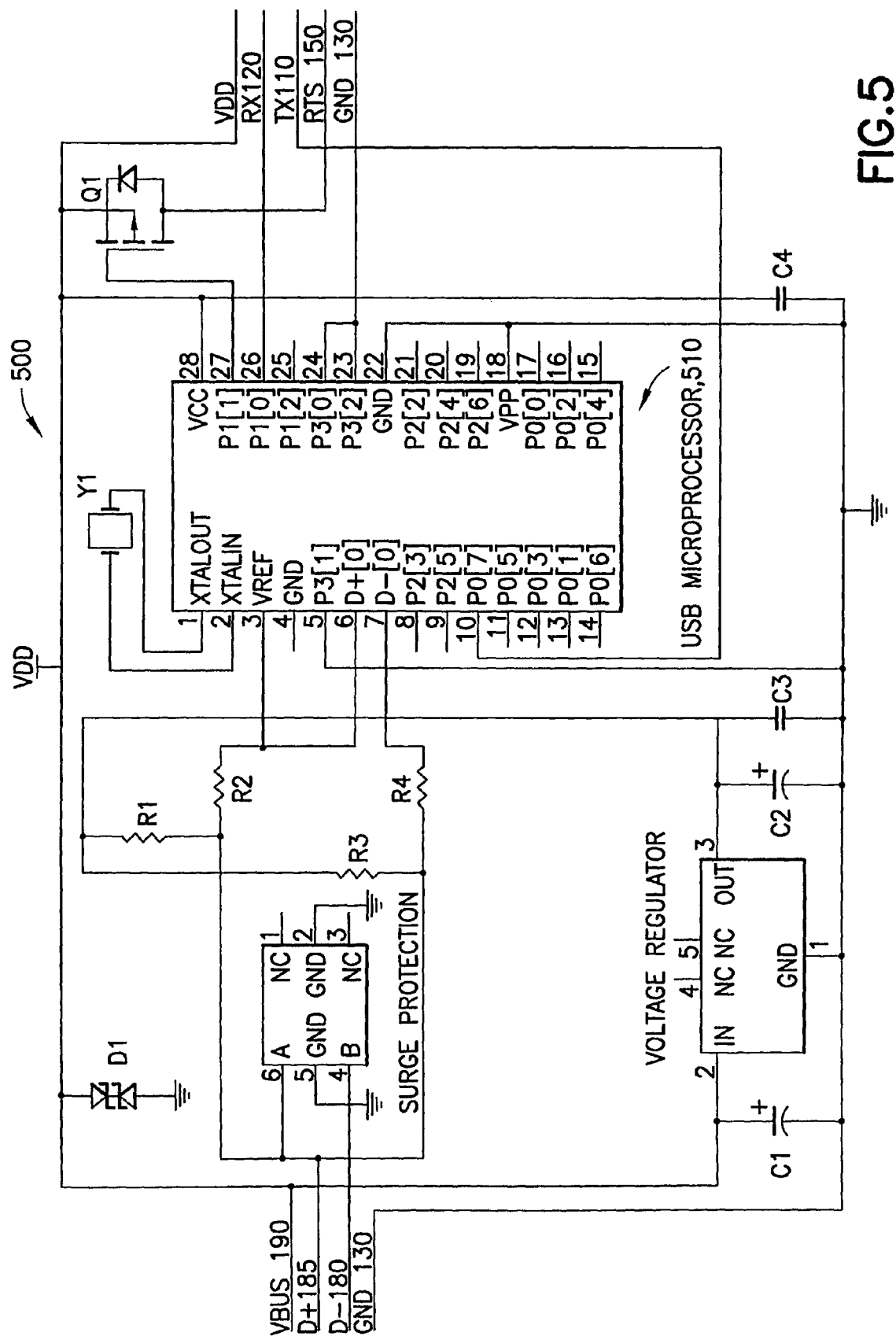
FIG. 5 shows exemplary USB connector circuitry shown in FIG. 3.

The isolation circuit 340 and 200 are substantially the same for either the Serial-to-Serial or the USB-to-Serial embodiment of the present invention; therefore, reference will be made to FIG. 4B. FIGS. 5 and 4B together form the circuit diagram of the cable shown in FIG. 3. In FIG. 5, VBUS 190 generates a regulated power supply voltage to power a microprocessor 510 used to convert USB data to serial data and vice versa. Microprocessor 510 software is used to direct the TX 110 signal back to the RX 120 signal or straight through to the TX 220 of the connected device. In FIG. 4B, RTS 150 also turns on and off an optical switch 155, which when enabled provides power to the isolated side of the cable. This causes battery power to be used by the medical device 30 because the medical device 30 is being signaled that the base device 20 is in a communication mode. By making the RTS 150 line low, base device 20 disables power to the section of the circuitry on the isolated side of the circuit that provides the communication mode signals. This is used due to the fact that the TX 210 line of the connected device is supplying power to the isolated side of the circuit, so the less circuitry powered the less draw on the connected device. The Schmidt triggered inverters 165, shown in FIG. 4B, are used to clean or sharpen the signals received across the isolation barrier in order to be received properly by either device 100', 200.

Figure 6:
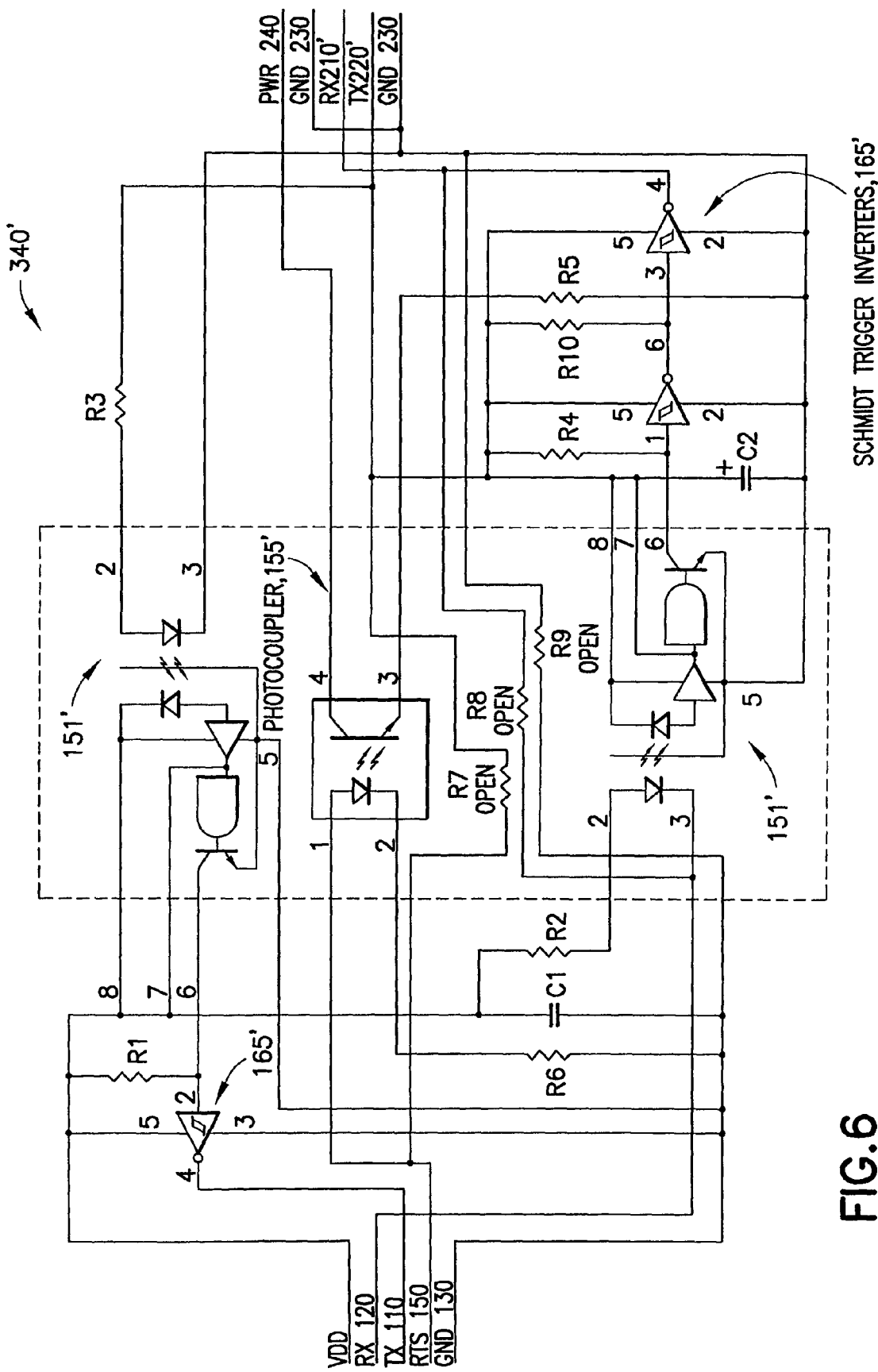
FIG. 6 shows an alternative circuit to the circuit shown in FIG. 4B according to an alternative embodiment of the present invention.

The cable 10 may also be implemented to operate as a full duplex cable by changing the connections to the photocoupler 155 within isolation barrier 340. As shown in FIG. 6, the TX 220' line from the medical device 30 is disconnected from the photocoupler 155' within isolation barrier 340'. The photocoupler 155' is directly powered by a dedicated power source 240. Power source 240 may either be internal to the medical device 30 or base device 20 or be external to both the medical 30 and base 20 devices. Power source 240 could be a battery or some other power supply. The RX 210' line will then be unaffected by the data being transmitted on TX 220'. The other circuit components, such as the optocouplers 151' and Schmidt trigger inverters 165', are the same as in FIG. 4B above.

Figure 7:
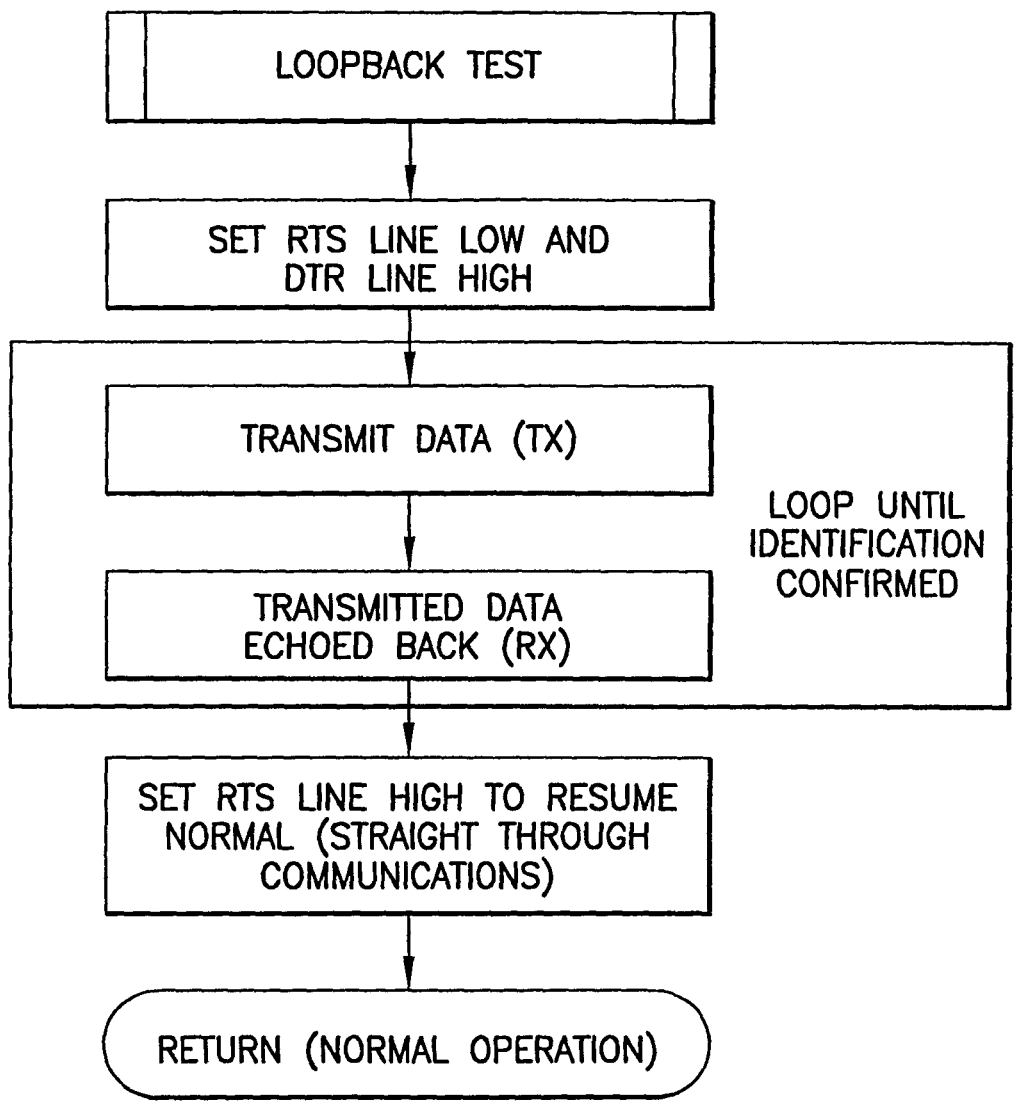
FIG. 7 shows a flowchart of a software loopback feature of an embodiment of the present invention as shown in FIGS. 2 and 3.

The software loopback program 330 shown in FIGS. 2 and 3 will now be described in further detail. Referring to FIG. 7, when the RTS 150 signal is low all data transmitted to the TX 110 line are directed, via hardware or software, to the RX 120 line on the non-isolated side of the circuit. If the cable is properly connected to the base device, the transmitted data is echoed back. Upon confirmation that the data echoed back is the data that was transmitted, RTS 150 is set high so that normal communications may resume. Such a capability is unique to the cable of the instant invention. This allows the PC software to poll the port when initiated to identify the cable constructed according to an embodiment of the present invention.

Figure 8:
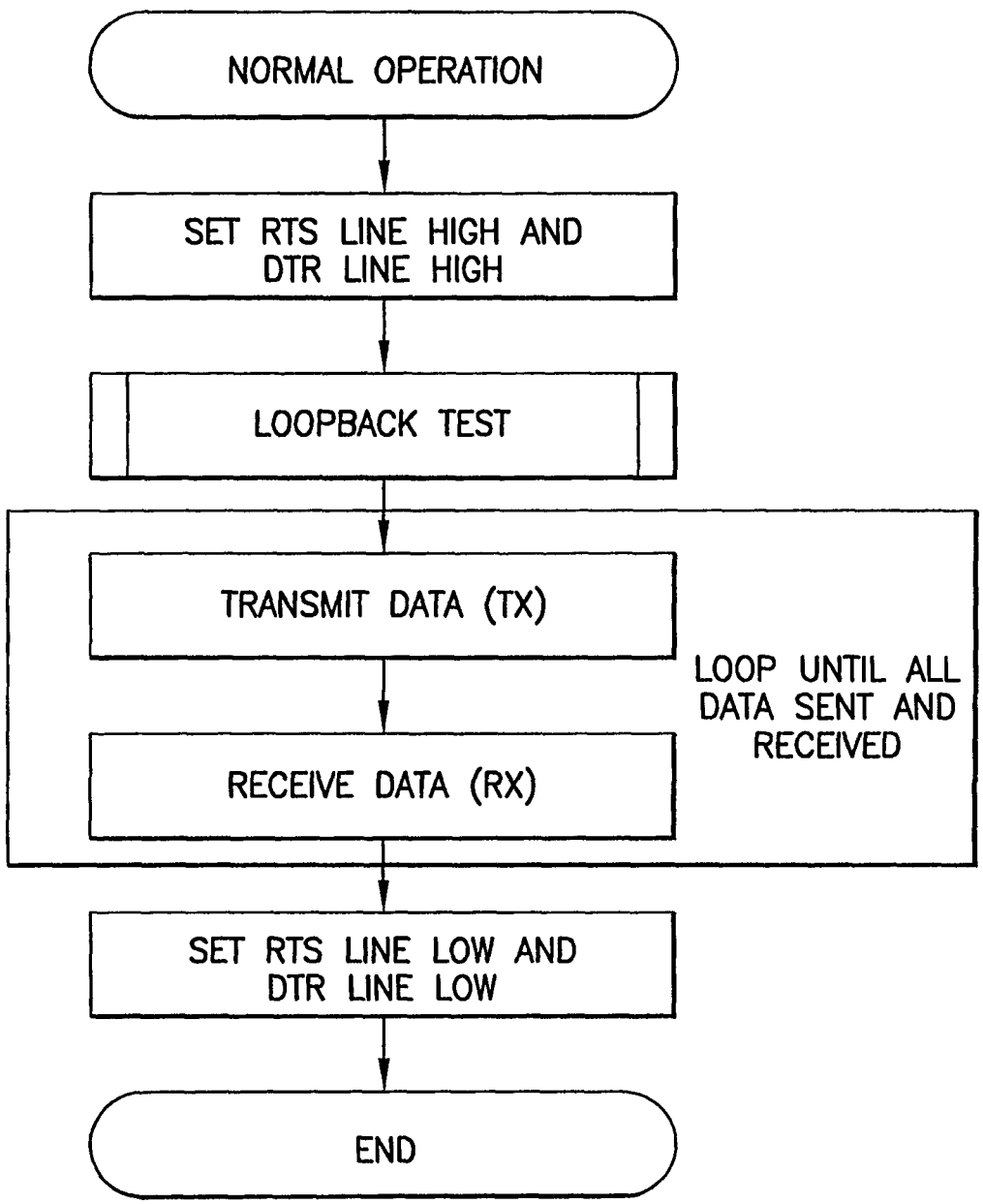
FIG. 8 shows a flowchart of the operation of the cable according to an embodiment of the present invention.

Overall, the present invention operates in the fashion shown in the flowchart of FIG. 8. When the base device 20 software applications starts it makes RTS line 150 and DTR lines 140 high in order to detect the serial cable on a port automatically. After this, RTS line 150 should be made low and DTR line 140 should be left high. This allows the software application in base device 20 to echo characters back in order to make sure cable 10 is connected to base device 20, and also powers down any unnecessary circuitry on the isolated side 200 of isolation barrier 340 to reduce the drain on battery within medical device 30. When base device 20 is ready to send data, base device 20 makes RTS line 150 high. Then base device 20 sends and receives data in a half duplex mode. Once the communication is complete, RTS line 150 should be made low in order to conserve battery power on medical device 30. If more data is requested later, the same procedure should be used. If done communicating, base device 20 makes DTR line 140 low.

There are several possible combinations of the design of cable 10 including the following permutations:
1. Self powered Serial-to-Serial with only the loopback feature.
2. Self powered Serial-to-Serial with only the isolation feature.
3. Self powered Serial-to-Serial with both the loopback and isolation feature.
4. Self powered USB-to-Serial with only the loopback feature.
5. Self powered USB-to-Serial with only the isolation feature.
6. Self powered USB-to-Serial with both the loopback and isolation feature.
7. All the above with full duplex.

Any combinations of the above are also possible, such as Serial-to-Serial and USB-to-Serial in the same device.

In order to assist the user in connecting a medical device 30 to a base device 20 using a cable 10 according to an embodiment of the present invention, the associated software detects a variety of connection states and causes the display of appropriate graphics and text messages.

In another embodiment of the present invention, the cable is accompanied with software that provides a graphical interface to assist the user in connecting the cable 10 to both the base device 20 and the medical device 30. In this case, the medical device 30 is a blood glucose meter and the base device 20 is a PC. An interface, such as a web browser interface, presents a Home Page from which the user may select to perform a number of functions. In particular, when a user selects the Meter Download and Print option from the Home Page, the software provides step by step graphical images, including text messages, of how the meter 30 and PC 20 should be connected. If a connection is not detected, an error message as well as graphics will be prominently displayed.

The operation of the software will now be described in more detail using the flowchart of FIG. 9 with corresponding graphics and text messages from FIG. 10. Referring to FIG. 9, the software first detects whether the interface cable is connected to the PC (S10). While it is detecting the cable 10, the graphic shows a colored question mark between the PC end of the cable graphic and the PC graphic with the text message, "Connecting" as shown in FIG. 10, message 2. If the cable 10 is connected to the PC 20, the graphics and text shown in FIG. 10, message 1 are displayed. These graphics show the PC end of the cable graphic touching the PC graphic with the text message, "PC Port Connected to Cable". The graphics and text shown in FIG. 10, message 3 is displayed if it is not connected. When the cable 10 is not connected to the PC, the graphic changes to show a red X between the PC end of the cable graphic and the PC 20 graphic and the text message, "Could not find connection on any port".

Referring back to FIG. 9, if the cable 10 is connected to the PC 20, the software then looks for a BD blood glucose meter 30. While it is detecting the meter (S20), the graphic shows a colored question mark between the meter end of the cable graphic and the meter graphic with the text message, "Identifying" as shown in FIG. 10, message 7. FIG. 10, message 8 shows the graphic and text message that is displayed when the base device 20 detects the meter 30, the graphic changes to show the meter end of the cable graphic touching the meter graphic with the text message, "Identified". If a meter is not detected, the graphic and text message of FIG. 10, message 4 is displayed, which shows a colored, preferably red, X between the meter end of the cable graphic and the meter graphic with the text message, "Could not identify meter on any port".

Once the meter is connected, the software then downloads the unique serial number from the meter and looks in the database for a match to an existing database record (S50). While it is performing this check, the graphic changes, as shown in FIG. 10, message 9, to show a graphic of small heads and a questions mark appearing over the meter with the text message, "Matching Meter to Assigned User". If no matching record is found in the database, the graphic changes to show a colored, preferably red, X in addition to the small heads with question mark graphic above the meter with the text message, "Unable to find meter user—Assign Meter User" as shown in FIG. 10, message 6. FIG. 10, message 10 shows the graphic and text that is displayed, if a matching record is found (S60), a small head graphic inside of the meter is displayed along with the text message, "Matched Assigned User to Meter."

Once a meter is assigned or a matching record is found, the software initiates the download of information from the meter (S70, S80, S90 and S100). While the data are downloading, the graphic changes as shown in FIG. 10, message 11, which displays a series of hatched lines moving from the meter to the PC. Once the download is complete, the graphic again changes to show a preferably a flashing diskette icon on the screen of the PC graphic with the text message, "Updating the Data." This graphics and text message changes to that shown in FIG. 10, message 12.

If any errors are detected by the software during the data download, the graphics and text message shown in FIG. 10, message 5 is displayed. The graphic and text message changes to show a colored, preferably red, X on the screen of the PC graphic and the meter color changes preferably to red with the text message, "The operation could not complete—Check the cable connection with the meter."

As described above, the graphical indication of both what is happening and what could be wrong if the connection is not working when making the physical connection between the blood glucose meter 30 and the PC 20 is accomplished through establishing a series of states that the software can detect. The graphical representations of these states are presented to the user through the display of the graphics and text messages.

The above graphics and text messages shown in FIG. 10 and associated with the specific actions shown in FIG. 9 are only exemplary and the invention should not be limited by them. Additionally, any type of graphic or text or combination thereof may be used as selected by one of ordinary skill in the art.

Each of the images and text-messages of FIG. 10 represent a discrete state of the connection and data downloading process. The following are the states that are represented:

| | |
|---|---|
| Idle | No activity |
| Connecting | Looking for available port connection |
| Connected | Port connection found |
| Identifying | Identifying meter |
| Identified | Meter identified |
| Matching | Matching meter with patient |
| Matched | Meter matched with patient |
| Downloading | Downloading data from meter |
| Updating | Updating database |
| ErrorConnecting | Error finding available port connection |
| ErrorIdentifying | Error identifying meter |
| ErrorMatching | Error matching meter to patient |
| ErrorDownloading | Error downloading data from meter |
| ErrorUpdating | Error updating database |
| ErrorUnexpected | unexpected/Undefined error |

Referring to FIG. 9, when the user starts a download the user interface component will load the protocol component (BDMeter) and asks it to find a meter connection (S10). BDMeter will enumerate COM1 through COM4 looking for a cable connection (S20). If a cable connection is found, then the protocol will attempt to identify a meter (S30). Enumeration of ports will stop at the first COM port located with a BD meter attached and that meter will be used.

Identification of the meter serial number will be dependent on the protocol implementation. In the case of BD, the "GETSETTINGS" command will be used to retrieve a serial number for the attached meter.

Once the meter is identified (S40), the meter download component will query the database to determine which patient is associated with the given meter (S50). If a match is made then the download will proceed for that patient, uninterrupted (S60). If a match cannot be found, the user will be prompted to select a patient to be associated with the meter or to enter a new patient to be associated with the meter. If the user selects a new or existing patient download will be performed for the so-selected patient. If the user cancels selection or creation of a patient, then the entire download operation will be aborted. If a database or other system related error occurs during association, the entire download session will be aborted.

Once a match is made, then the glucose values will be downloaded (S70), verified and saved (S80) in the database. Then insulin values will be downloaded (S90) and saved (S100) in the database. The database update will not update values that already exist for the given meter, date and time.

An entire download will be treated as a discrete transaction, it either succeeds completely or it fails. If any errors occur during the glucose download (S70), no values will be stored. Similarly, if any errors occur during the insulin download (S90), no values will be stored.

The download interface program is preferably written in a combination of C++ programming language and Assembly language. The Home Page is preferably written in HTML programming language. The charts, graphs, and forms are preferably written in C++ and Visual Basic. Of course, one of ordinary skill may use other programming languages and the invention should not be limited by the use of these programming languages.

The meter download process is divided into three distinct layers: User Interface, Protocol and Communications. The purpose of this design is to facilitate handling different meters, download protocols and communications mechanisms in the future and to provide a generic data exchange format between the user interface layer and the protocol layer:

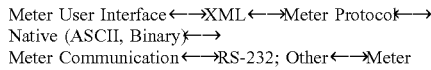

BD.MeterControl will provide an ActiveX control implementation of the meter download user interface. It provides a single button allowing the user to initiate a download and displays images to depict the various states of the download. The BD.MeterControl implements the IBDObject interface and handles the following messages:

| | |
|---|---|
| BDOP_PRESHOW | Moves to IDLE state |
| EDOP_PREHIDE | Prompts the user if it is alright to close the view, if a download is in progress. |
| BDOP_PRINT | Handler for print requests. |

As explained above, FIG. 9 shows the processes that execute when the user initiates a download from the Meter tab. Each state detection step has an associated reference number that refers to the numbered images.

While the invention herein disclosed has been described by means of specific embodiments and applications thereof, numerous modifications and variations could be made thereto by those skilled in the art without departing from the scope of the invention set forth in the claims.

We claim:

1. A system for connecting a glucose monitor to a base device comprising:
a base device and a glucose monitor; and
a detachable cable comprising a detachable serial port connector at a first end and a detachable second connector at a second end, wherein:
the serial port connector detachably connects said first end of said cable to said base device; and
the second connector detachably connects said second end of said cable to said glucose monitor;
the detachable cable further comprising:
an optical isolation circuit between said first end and said second end of said cable that prevents electrical signals from propagating to the glucose monitor from the base device via said cable; and
a loopback circuit on a base device side of the optical isolation circuit that provides a loopback signal to a connected one of a plurality of serial ports of said base device to identify to which of said plurality of serial ports said cable is connected;
wherein the loopback circuit echoes data received from a serial output of the base device to a serial input of the base device; and
wherein the base device comprises a display adapted to graphically display a first connection state of the connection of the serial port connector of the detachable cable to the base device, and a second connection state of the connection of the second connector of the detachable cable to the glucose monitor, said first and second connection states being displayed separately and simultaneously, and to animatedly display a transfer of data between the glucose device and the base device.

2. A cable as claimed in claim 1
wherein said optical isolation circuit receives electrical power from a power supply in said base device.

3. A medical system comprising a detachable cable, a glucose monitor and a base device, wherein the detachable cable comprises a detachable serial port connector at first end and a detachable second connector at a second end, wherein the
the serial port connector detachably connects said first end of said cable to said base device; and
the second connector detachably connects said second end of said cable to said glucose monitor;
the detachable cable further comprising:
an optical isolation circuit between said first end and said second end of said cable that prevents electrical signals from propagating to the glucose monitor from the base device via said cable;
wherein said optical isolation circuit receives electrical power from a power supply in said base device;
and wherein said cable further comprises a loopback circuit provided on a base device side of the optical isolation circuit that provides a loopback signal to a connected one of a plurality of serial ports of said base device to identify to which of said plurality of serial ports said cable is connected;
wherein the loopback circuit echoes data received from a serial output of the base device to a serial input of the base device; and
wherein the base device comprises a display adapted to graphically display a first connection state of the connection of the serial port connector of the detachable cable to the base device, and a second connection state of the connection of the second connector of the detachable cable to the glucose monitor, said first and second connection states being displayed separately and simultaneously, and to animatedly display a transfer of data between the glucose device and the base device.

4. A medical system as claimed in claim 3 further comprising:

wherein said loopback circuit provides said loopback signal to the base device in response to signals received from the base device;

said loopback signal is interpreted by the base device, and a graphical display related to the interpreted loopback signal is presented to the user.

5. A medical system as claimed in claim 4, wherein said loopback signal provided by said loopback circuit to the base device enable said graphical display to indicate connection points where said cable has not made a proper connection to the base device, the medical device, or both.

6. A cable as claimed in claim 1, wherein said serial port connector is a Universal Serial Bus connector.

7. A cable as claimed in claim 1, wherein said serial port connector is a RS-232C connector.

8. The cable as claimed in claim 1, wherein said optical isolation circuit receives power from said base device.

9. A cable as claimed in claim 8, wherein power is removed from the optical isolation circuit after a predetermined condition is satisfied.

10. A cable as claimed in claim 9, wherein said predetermined condition is satisfied when all the required data has been transferred between the glucose monitor and the base device.

11. A medical system comprising a detachable cable, a glucose monitor and a base device, wherein the detachable cable comprises a detachable serial port connector at a first end and a detachable second connector at a second end, wherein:
the serial port connector detachably connects said first end of said cable to said base device; and
the second connector detachably connects said second end of said cable to said glucose monitor;
the detachable cable further comprising:
an optical isolation circuit between said first end and said second end of said cable that prevents electrical signals from propagating to the glucose monitor from the base device via said cable; and
a loopback circuit on a base device side of the optical isolation circuit that provides a loopback signal to a connected one of a plurality of serial ports of said base device to identify to which of said plurality of serial ports said cable is connected;
wherein the loopback circuit echoes data received from a serial output of the base device to a serial input of the base device;
wherein said optical isolation circuit receives power from said base device;
wherein power is removed from the optical isolation circuit after a predetermined condition is satisfied;
wherein power provided to said cable from the glucose monitor is reduced after said predetermined condition is satisfied; and
wherein the base device comprises a display adapted to graphically display a first connection state of the connection of the serial port connector of the detachable cable to the base device, and a second connection state of the connection of the second connector of the detachable cable to the glucose monitor, said first and second connection states being displayed separately and simultaneously, and to animatedly display a transfer of data between the glucose device and the base device.

12. A cable as claimed in claim 11, wherein said serial port connector is a Universal Serial Bus connector.

13. A cable as claimed in claim 11, wherein said serial port connector is a RS-232C connector.

14. A medical system comprising a detachable cable, a glucose monitor and a base device, the detachable cable detachably connecting the glucose monitor to the base device, the detachable cable comprising a detachable serial port connector at a first end and a detachable second connector at a second end, wherein:
the detachable serial port connector at said first end of the cable connects to one of a plurality of serial ports in said base device; and
the detachable connector at said second end connects to said glucose monitor;
the detachable cable further comprising:
an optical isolation circuit between said first end and said second end of said cable that prevents electrical signals from propagating to the glucose monitor from the base device via said cable; and
a loopback circuit on a base device side of the optical isolation circuit that receives a loopback signal from the connected one of said plurality of serial ports of said base device to identify to which of said plurality of serial ports said glucose monitor is connected;
wherein the loopback circuit echoes data received from a serial output of the base device to a serial input of the base device; and
wherein the base device comprises a display adapted to graphically display a first connection state of the connection of the serial port connector of the detachable cable to the base device, and a second connection state of the connection of the second connector of the detachable cable to the glucose monitor, said first and second connection states being displayed separately and simultaneously, and to animatedly display a transfer of data between the glucose device and the base device.

15. A cable as claimed in claim 14 wherein said loopback circuit receives data from the connected one of said plurality of serial ports of said base device, and returns said data to said base device via said connected one of said plurality of serial ports to confirm said medical device is connected to said one of said plurality of serial ports of said base device via said cable.

16. A cable as claimed in claim 15, wherein said base device comprises a graphical display, and said base device provides graphical feedback on said display based on said returned data from said loopback circuit to display to a user whether the glucose monitor is connected to said base device or to said cable.

17. A cable as claimed in claim 14, wherein when power is removed from said loopback circuit said medical device is enabled to transmit data relating to a medical condition to the base device.

18. A cable as claimed in claim 14, wherein power is removed from the optical isolation circuit which reduces the amount of power provided to the cable by the glucose monitor.

19. A cable as claimed in claim 14, wherein said serial port connector is a Universal Serial Bus connector.

20. A cable as claimed in claim 14, wherein said serial port connector is a RS-232C connector.

21. The cable of claim 1, wherein the loopback circuit echoes data when an RTS line is low.

22. The cable of claim 1, wherein a photocoupler of the cable is powered down when an RTS line is low.

23. The cable of claim 1, wherein a non-isolated base device side of the cable is powered when an RTS line is high.

* * * * *